United States Patent [19]

Theis et al.

[11] Patent Number: 5,777,152

[45] Date of Patent: Jul. 7, 1998

[54] PROCESS FOR PREPARING 2-ARYL-2-CHLOROMALONIC DIESTERS

[75] Inventors: Christoph Theis, Niederkassel; Radu Bordeianu, Marl; Wilfried Latz, Niederkassel, all of Germany

[73] Assignee: Huels Aktiengesellschaft, Marl, Germany

[21] Appl. No.: 610,055

[22] Filed: Feb. 29, 1996

[30] Foreign Application Priority Data

Mar. 15, 1995 [DE] Germany .................. 195 09 377.1

[51] Int. Cl.$^6$ .................................................. C07C 69/38
[52] U.S. Cl. ............................................................ 560/82
[58] Field of Search .................................... 560/82, 83

[56] References Cited

U.S. PATENT DOCUMENTS 5,502,125  3/1996  Bordeianu et al. .

FOREIGN PATENT DOCUMENTS 1 948 475  5/1970  Germany .

44 20 263  12/1995  Germany .

OTHER PUBLICATIONS

CA111:96297—Tetrahedron Lett (1989) 30(10) 1289–92 Oxidative deprot. of carbonyl comp by iron salts.

CA110:38696 J Chem Res Synop (1985) 5 156–7 Abst. Citterio Side oxidation of aryl malonates by manganese(3)acetate.

Cotton and Wilkinson "Advanced Inorganic Chemistry" 3rd edition pp. 472–479 (1972).

Journal of the Chemical Society, pp. 1607–1616, 1928, B. Fluerscheim, et al., "The Laws of Aromatic Substitution. Part VIII".

*Primary Examiner*—C. Warren Ivy
*Assistant Examiner*—Jean F. Vollano
*Attorney, Agent, or Firm*—Oblon, Spivak, McLelland, Maier & Neustadt, P.C.

[57] ABSTRACT

2-Aryl-2-chloramalonic diester is prepared by reacting 2-arylmalonic diesters with aqueous hypochlorite in the presence of an inert solubilizer at pH 8 to 14.

13 Claims, No Drawings

PROCESS FOR PREPARING 2-ARYL-2-CHLOROMALONIC DIESTERS

BACKGROUND OF THE INVENTION

1 Field of the Invention

The present invention relates to a process for preparing 2-aryl-2-chloromalonic diesters from 2-aryl-malonic diesters.

2 Description of the Background

2-Aryl-2-chloromalonic diesters can be employed as disclosed in German Patent Application No. DE P 44 15 872.6 as highly active activators in the preparation of ethylene copolymers.

Various methods have already been disclosed for preparing 2-aryl-2-chloromalonic diesters. Thus, Flurscheim, J. Chem. Soc. 1928, 1607–16, discloses diethyl 2-chloro-2-phenylmalonate in moderate yield by reacting diethyl 2-phenylmalonate with dry chlorine gas in carbon tetrachloride at 0°C. Robert, Tetrahedron 42, 2275–81 (1986), discloses the preparation of 2-chloro-2-phenylmalonic diesters by reacting geminal dicyano compounds with hydrogen chloride. Citterio, J. Chem. Research (S), 156–157 (1988), describes the oxidation of 2-phenylmalonic diesters with manganese (III) acetate in the presence of chloride ions thereby preparing 2-chloro-2-phenylmalonic diesters.

Common to all the processes described in the literature is that the yields and purities of the desired products are usually unsatisfactory and some of the starting materials are difficult and complicated to obtain. In addition, use is sometimes made of chlorinating agents which, because of their nature or their reaction products which form in the desired reaction, are not very suitable for industrial manufacture of the desired compounds from a process, economic and ecological viewpoint. A need therefore continues to exist for a method of preparing 2-aryl-2-chloromalonic diesters in improved yields.

SUMMARY OF THE INVENTION

Accordingly, one object of the invention is to provide a technically simple, economical and above all productive process for preparing 2-aryl-2-chloromalonic diesters from the corresponding and conveniently prepared 2-arylmalonic diesters.

Briefly, this object and other objects of the present invention as hereinafter will become more readily apparent can be attained by reacting 2-aryl-malonic diesters with aqueous hypochlorite in the presence of an inert solubilizer at pH 8 to 14.

DETAILED DESCRIPTION OF THE PREFERRED EMBODIMENTS

The product 2-aryl-2-chloromalonic diesters have formula I:

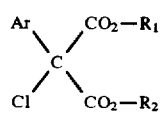

wherein $R_1$ and $R_2$ are, independently of one another, straight-chain or branched alkyl having from 1 to 6 carbon atoms, cycloalkyl or aralkyl. Ar is aryl, preferably phenyl, each Ar radical bearing one or more alkyl radicals having from 1 to 4 carbon atoms or halogen atoms.

In the 2-arylmalonic diesters of formula II:

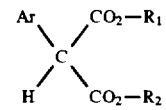

wherein the substituents $R_1$, $R_2$ and Ar are as defined above.

For the purposes of the present invention, aqueous hypochlorite is an aqueous solution or aqueous suspension of salts of hypochlorous acid. Alkaline earth metal hypochlorites are usually used as a suspension and alkali metal hypochlorites are used as a solution. Suitable examples include calcium, barium, sodium and potassium salts. Preference is given to using alkali metal hypochlorite solutions in the reaction.

Suitable solubilizers which are inert under the given reaction conditions are acetonitrile, propionitrile and butyronitrile. Preferred is acetonitrile.

It is also possible to use other auxiliary solvents, for example, solvents which are immiscible with water. The amount of solubilizer to be used is not critical per se, since at the end of the reaction a readily separable 2-phase mixture generally results and the solubilizer can be very easily recovered from both the organic and aqueous phases obtained, for example by distillation, and can be recycled without further purification.

The reaction of the invention can be shown as follows in the instance sodium hypochlorite solution is employed in the reaction:

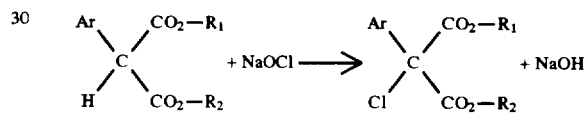

It has surprisingly been found that in order to obtain a high yield of 2-aryl-2-chloromalonic diester and to high product purity, it is essential that the metal hydroxide liberated in the reaction should be buffered by means of an acid. Preferably, the reaction is conducted at a pH of from 11 to 14.

Suitable acid buffering agents include mineral acids, which may be diluted, such as hydrochloric, sulfuric and phosphoric acid; gaseous acids, such as, for example, hydrogen chloride and carbon dioxide; organic acids such as formic acid and mono-, di- and trichloroacetic acid and mono-, di- and trichloropropionic acid and also aromatic carboxylic acids which may be diluted with water and which may bear one or more inert substituents.

It has further been found that low reaction temperatures favorably influence the yields which can be achieved, as well as product purities. The reaction is therefore advantageously carried out in the temperature range from 0° to 50° C., preferably in the temperature range from 2° to 25° C. This temperature range temperature ensures a rapid and gentle reaction of the starting materials used. However, the use of even lower temperatures is also possible.

In the chlorination of 2-arylmalonic diesters with hypochlorite, a molar ratio of 1:1 is normally used. However, hypochlorite is advantageously used in excess. The 2-arylmalonic diester/hypochlorite molar ratio is normally in the range from a 1:1 to 1:5. The ratio preferably ranges from 1:1 to 1:2 and most preferably from 1:1.05 to 1:1.2. After the end of the reaction, any amount of hypochlorite still present can be destroyed in a manner known per se, for instance by addition of aqueous sodium sulfite.

The process of the invention gives the 2-aryl-2-chloromalonic diesters in high yield and high purity. The chemicals required for this purpose are inexpensive, easy to handle and physiologically acceptable.

The process of the invention can be carried out, for example, by initially charging the hypochlorite in the form of an aqueous solution or suspension and metering in the starting material, if desired diluted with the inert solubilizer, while keeping the pH range constant by parallel metering in of an acid, with the metering in of acid being continued even in the post-reaction phase in order to maintain the selected pH range. However, it is also possible to carry out the process by first adding the inert solubilizer to the initially charged hypochlorite and then metering in the undiluted starting material while keeping the pH constant. Another possibility is to meter in the starting material and selected acid together, if desired in conjunction with the solubilizer. However, it is also possible to choose an inverse procedure in which starting material and solubilizer are initially charged and hypochlorite solution and acid are metered in parallel.

In general, the reactions result in a 2-phase reaction mixture from which the organic phase can easily be separated. The organic phase obtained generally contains the major part of the inert solubilizers used. These can be separated therefrom, as also from the remaining aqueous phase, by means of a simple distillation.

The desired product is likewise obtained in high-purity in a manner known per se, for example by fractional vacuum distillation.

Having generally described this invention, a further understanding can be obtained by reference to certain specific examples which are provided herein for purposes of illustration only and are not intended to be limiting unless otherwise specified.

EXAMPLE 1

A 217.8 g amount of aqueous sodium hypochlorite solution (content: 8.55% of NaOCl corresponding to 500 mmol of NaOCl) is cooled to 12° C. The pH of the solution is adjusted to about 13 by addition of aqueous 20% strength hydrochloric acid. To this cooled initial charge, 65.0 g of acetonitrile are added and then 106.2 g of diethyl 2-phenylmalonate (450 mmol) are added dropwise over the course of about 30 minutes, with the pH of the reaction mixture being kept in the range from 13.9 to 13.2 by simultaneous metering in of the aqueous 20% strength hydrochloric acid and the internal temperature being kept at about 12° C. by cooling.

After the metering in of malonic ester is complete, the mixture is allowed to react further for about 120 minutes while the pH range is kept constant. Excess hypochlorite present is then destroyed by addition of sodium sulfite. The organic phase is separated from the resulting 2-phase mixture.

After evaporation of the organic phase, the resulting residue is subjected to flash vacuum distillation, giving 116.4 g of diethyl 2-chloro-2-phenylmalonate having a boiling point of 106°–8° C. (0.2 hPa). This corresponds to a yield of 95.6% of theory. The purity of the product, determined by gas chromatography, is ≧98.5% (starting material content: ≦0.3%).

EXAMPLE 2

The procedure of Example 1 is repeated, but the initial and reaction pH range is from 11.0 to 11.2.

After an analogous work-up procedure, 110.0 g of distillate are obtained. This corresponds to a yield of 91.1% of theory. The product purity determined by GC is 95.3% (starting material content: 3.7%).

EXAMPLE 3

The procedure of Example 1 is repeated, but using 131.4 (450 mmol) of di-n-butyl 2-phenymalonate and 100.0 g of acetonitrile. The metering time of starting material is about 60 minutes.

The acetonitrile-free crude product obtained by analogous work-up is subjected to a fractional vacuum distillation through a 20 cm Vigreux column. This gives 128.9 g of di-n-butyl 2-chloro-2-phenylmalonate having a boiling point of 128°–30° C. (0.2 hPa). This corresponds to a yield of 80.8% of theory, purity (GC): >98%.

EXAMPLE 4

The procedure of Example 3 is repeated using 118.0 g (450 mmol) of di-n-propyl 2-phenylmalonate. The metering time for starting material is about 120 minutes. The initial and reaction pH range is 13.4–13.6. The product obtained in an analogous manner is worked up as in Example 3. A 124.7 g amount (84.9% yield) of di-n-propyl 2-chloro-2-phenylmalonate having a purity determined by GC of >98% is obtained.

EXAMPLE 5

The procedure of Example 4 is repeated except that 93.6 g (450 mmol) of dimethyl 2-phenylmalonate in admixture with 100.0 g of acetonitrile is metered into the reaction over the course of about 2 hours. Work-up using a method similar to Example 3 gives 94.2 g of pure product, and the yield of dimethyl 2-chloro-2-phenylmalonate corresponds to 86.3% of theory, purity: >98%.

EXAMPLE 6

The procedure of Example 1 is repeated except that 120.0 g of acetonitrile and 112.5 g (475 mol) of diethyl 2-(p-tolyl)malonate are used. The post-reaction time is 2.5 hours at about 15° C. The acetonitrile-free crude product obtained after analogous work-up is purified by distillation as described in Example 3. A 119.8 g amount of diethyl 2-chloro-2-(p-tolyl)malonate (purity: >98.5%) is obtained, which is equivalent to a yield of 92.9% of theory.

EXAMPLE 7

The procedure of Example 6 is repeated except that 121.7 g (450 mmol) of diethyl 2-(p-chlorophenyl)malonate is used. A 130.9 g amount of diethyl 2-chloro-2-(p-chlorophenyl)malonate (purity: >98%) is obtained, which is equivalent to a yield of 95.4% of theory.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing 2-aryl-2-chloromalonic diesters from 2-arylmalonic diesters, comprising: reacting 2-arylmalonic diesters with aqueous hypochlorite in the presence of an inert nitrile solubilizer at pH 8 to 14.

2. The process according to claim 1, wherein the reaction is carried out with an aqueous alkali metal hypochlorite solution.

3. The process according to claim 1, wherein the reaction is carried out at pH 11 to 14.

4. The process according to claim 1, wherein the reaction is carried out at a temperature of from 0° to 50° C.

5. The process according to claim 4, wherein said temperature ranges from 2° to 25° C.

6. The process according to claim 1, wherein arylmalonic diester and hypochlorite are reacted in a molar ratio of 1:1 to 1:5.

7. The process according to claim 6, wherein the molar ratio is from 1:1 to 1:2.

8. The process according to claim 7, wherein said molar ratio ranges from 1:1.05 to 1:1.2.

9. The process according to claim 1, wherein said solubilizer is acetonitrile, propionitrile or butyronitrile.

10. The process according to claim 9, wherein the solubilizer is acetonitrile.

11. A process for preparing 2-aryl-2-chloromalonic diesters from 2-arylmalonic diesters, comprising:

reacting 2-arylmalonic diesters with aqueous hypochlorite in the presence of an inert solubilizer and continually adding acid throughout the reaction in order to maintain the pH of the reaction mixture to within the range of 8–14.

12. The process of claim 11, wherein said pH ranges from 11.0–13.9.

13. The process of claim 11, wherein said inert solubilizer is a nitrile solubilizer.

* * * * *